(12) United States Patent
Piletsky et al.

(10) Patent No.: US 12,025,579 B2
(45) Date of Patent: Jul. 2, 2024

(54) ELECTROCHEMICAL SENSOR

(71) Applicant: UNIVERSITY OF LEICESTER, Leicester (GB)

(72) Inventors: Sergey Piletsky, Leicester (GB); Francesco Canfarotta, Leicester (GB); Antonio Guerreiro, Leicester (GB); Giovanna Marrazza, Florence (IT); Riccardo Rapini, Florence (IT)

(73) Assignee: UNIVERSITY OF LEICESTER, Leicester (GB)

( * ) Notice: Subject to any disclaimer, the term of this patent is extended or adjusted under 35 U.S.C. 154(b) by 833 days.

(21) Appl. No.: 16/979,924

(22) PCT Filed: Mar. 12, 2019

(86) PCT No.: PCT/GB2019/050687
§ 371 (c)(1),
(2) Date: Sep. 11, 2020

(87) PCT Pub. No.: WO2019/175565
PCT Pub. Date: Sep. 19, 2019

(65) Prior Publication Data
US 2021/0010968 A1     Jan. 14, 2021

(30) Foreign Application Priority Data
Mar. 13, 2018  (GB) ..................................... 1803997

(51) Int. Cl.
*G01N 27/327*  (2006.01)
*C12Q 1/00*    (2006.01)

(52) U.S. Cl.
CPC ......... *G01N 27/3271* (2013.01); *C12Q 1/004* (2013.01); *G01N 2600/00* (2013.01)

(58) Field of Classification Search
None
See application file for complete search history.

(56) References Cited

U.S. PATENT DOCUMENTS

| 5,271,819 A | 12/1993 | Bockowski |
| 5,356,786 A | 10/1994 | Heller et al. |

(Continued)

FOREIGN PATENT DOCUMENTS

| CN | 17436318 A | 12/2017 |
| CN | 107436318 A | 12/2017 |
| WO | 2015130529 A3 | 9/2015 |

OTHER PUBLICATIONS

S. Brahim, et al., "Interferent Suppression Using a Novel Polypyrrole-Containing Hydrogel in Amperometric Enzyme Biosensors", Electroanalysis, 14(9): p. 627-633, May 2002.*

(Continued)

*Primary Examiner* — J. Christopher Ball
(74) *Attorney, Agent, or Firm* — BioPharma Law Group, PLLC (57) ABSTRACT

The application provides a method of detecting an analyte in a sample. The method comprises disposing a binding agent in an electrochemical compartment. The binding agent is configured to bind to an interfering species. The method further comprises disposing a solution comprising a sample in the electrochemical compartment. The sample comprises an analyte and the interfering species. The method then comprises applying a voltage across first and second spaced apart electrodes disposed in the solution, and thereby causing a current to flow through the solution between the electrodes. Finally, the method comprises measuring the current and/or voltage and thereby detecting the analyte.

21 Claims, 4 Drawing Sheets

(56) References Cited

U.S. PATENT DOCUMENTS

| | | |
|---|---|---|
| 6,807,842 B2 | 10/2004 | Williams et al. |
| 9,134,305 B2 | 9/2015 | Cai et al. |
| 9,234,864 B2 | 1/2016 | Heller et al. |
| 2004/0126814 A1 | 7/2004 | Singh et al. |
| 2005/0176136 A1 | 8/2005 | Burd et al. |
| 2009/0050477 A1 | 2/2009 | Catt et al. |
| 2016/0209420 A1 | 7/2016 | Barnes et al. |

OTHER PUBLICATIONS

Communication Pursuant to Article 94(3) EPC dated Dec. 1, 2022, EP Application No. 19713137.8, pp. 1-6.

Cheng Xue et al., "Amperometric detection of dopamine in human serumby electrochemical sensor based on gold nanoparticles doped molecularly imprinted polymers." Biosensors and Bioelectronics 49 (2013): 199-203.

Joseph Wang, "Electrochemical Glucose Biosensors," Chemical Reviews, vol. 108, No. 2, 2008, pp. 814-825.

T. Gregory Drummond et al., "Electrochemical DNA Sensors," Nature Biotechnology, vol. 12, No. 10, Oct. 2003, pp. 1192-1199.

Karl Cammann et al., "Fast chromatographic separation techniques as competitors to chemical and biochemical sensor systems," Fresenius' Journal of Analytical Chemistry, vol. 349, 1994, pp. 338-345.

Igor Volov et al., "Chromatography of bis-(3-sulfoporpyl) disulfide and its breakdown products by HPLC coupled with electrochemical detection," Journal of Separation Science, vol. 34, No. 18, 2011, pp. 2385-2390.

Satoshi Koide et al., "Determination of human serum 8-hydroxy-2-deoxyguanosine (8-OHdG) by HPLC-ECD combined with solid phase extraction (SPE)," Journal of Chromatography B, vol. 878, 2010, pp. 2163-2167.

Emil Palecek et al., "Magnetic beads as versatile tools for electrochemical DNA and protein biosensing," Talanta, vol. 74, No. 3, pp. 276-290.

D.J. Daly et al., "The use of polymers coupled with metallised electrodes to allow H2O2 detection in the presence of electrochemical interferences," Talanta, vol. 49, 1999, pp. 667-678.

Francesco Canfarotta et al., "Solid-phase synthesis of molecularly imprinted nanoparticles," Nature Protocols, vol. 11, No. 3, 2016, pp. 443-455.

GB Search Report dated Sep. 13, 2018, GB Application No. 1803997.4, pp. 1-4.

PCT International Search Report and Written Opinion dated Jun. 14, 2019, PCT Application No. PCT/GB2019/050687, pp. 1-13.

Charlie O. Parker et al., "Development of an electrochemical immunosensor for aflatoxin M1 in milk with focus on matrix interference", Biosensors and Bioelectronics, vol. 24, Issue 8, Apr. 2009, pp. 2452-2457.

Examination report No. 2 for standard patant application dated Apr. 4, 2024, Australian Application No. 2019233794.

T. Madrakian, et al "Construction a magneto carbon paste electrode usng synthesized molecularly imprinted magnetic nanospheres for selective and sensitive determinatian of mefenamic acid in some real samples", Biosensors and Bioelectronics, vol. 68, 2015, pp. 712-718.

Batlokwa, B.S., at al, "A Novel Molecularly imprinted Polymer for the Selective Removal of Chlorophyll from Heavily Pigmented Green Plant Extracts prior to Instrumental Analysis", Journal of Chemistry, vol. 2013, Article ID 540240, 4 pages.

Tabane, T. H. et al, "A Novel Molecularly imprinted Polymer for the Selective Removal of Interfering Hemoglobin Prior to Whole Blood Analysis", Biochemistry & Analytical Biochemistry, vol. 6, Issue 2, 2017.

* cited by examiner

ELECTROCHEMICAL SENSOR

CROSS REFERENCE TO RELATED APPLICATIONS

This application is a National Stage of International Application No. PCT/GB2019/050687 filed on Mar. 12, 2019, which claims priority to GB Application No. 1803997.4 filed on Mar. 13, 2018. The contents of the above applications are incorporated herein by reference in their entirety.

The present invention relates to a method and kit for detecting an analyte in a sample. The method and kit are configured to reduce a signal from an interfering species which may be present in the sample.

Electrochemical techniques for detecting the presence of analyte in a sample have been described (1-8). When using electrochemical assays or sensors, an enduring challenge has been to remove interfering substances that generate signals of similar nature that obscure the analyte detection. Typically, this is achieved by using sample pre-treatment procedures such as solid-phase extraction or some other forms of chromatography (9-12). However, this increases the costs of analysis and the time it takes.

It is therefore desirable to provide a sensor which suppresses signals from interfering species in the sample. Only one example of interferent-suppressing sensor has been reported to date (13). This relies on the electropolymerisation of a non-conductive polymer on the surface of electrodes. The polymer employed allows selective detection of $H_2O_2$ based on 'sieving' properties of charge and size. However, this method can only be used if the analyte of interest is hydrogen peroxide.

Accordingly, the present invention arises from the inventors work in attempting to overcome the problems associated with the prior art.

In accordance with a first aspect of the invention, there is provided a method of detecting an analyte in a sample, the method comprising:
   disposing a binding agent in an electrochemical compartment, wherein the binding agent is configured to bind to an interfering species;
   disposing a solution comprising a sample in the electrochemical compartment, wherein the sample comprises an analyte and the interfering species;
   applying a voltage across first and second spaced apart electrodes disposed in the solution, and thereby causing a current to flow through the solution between the electrodes; and
   measuring the current and/or voltage and thereby detecting the analyte.

Advantageously, the binding agent supresses the electrochemical signal of the interfering species. Accordingly, the analyte can be accurately detected without pre-treatment of the sample being required enabling detection to be conducted quickly and cheaply. Furthermore, a suitable binding agent can be provided to block any identified interfering species which would otherwise interfere with the signal from the analyte. The binding agent can even bind to an interfering species that has similar structure and chemical properties to analyte.

It may be appreciated that the binding agent may be disposed in the solution prior to the solution being disposed in the electrochemical compartment. Accordingly, the binding agent will be transferred to the electrochemical compartment at the same time as the solution.

Alternatively, the binding agent may be disposed in the electrochemical compartment before or after the solution is disposed therein. Preferably, the binding agent is disposed in the electrochemical compartment the solution is disposed therein. However, both the binding agent and the solution should be disposed in the electrochemical compartment before the voltage is applied across the electrodes.

Preferably, the method comprises measuring the current and/or the voltage, and thereby detecting the concentration of the analyte in the solution.

In one embodiment, the method comprises measuring the current, and thereby detecting the analyte. Preferably, the method comprises measuring the current, and thereby detecting the concentration of the analyte in the solution.

The binding agent may comprise a molecularly imprinted polymer (MIP), an antibody or a fragment thereof, an aptamer, an affimer, a lectin, a peptide, a protein, a macrocyclic ligand or an organic molecule. The MIP may comprise a film, a microparticle or a nanoparticle, or a non-crosslinked system, such as a linear MIP. The protein may comprise a natural or artificial protein. The artificial protein may comprise an affitin, a DARPin or an affibody. Advantageously, an electrochemical signal from interfering species is suppressed because the MIP, antibody, aptamer or affimer bind by enfolding the interfering species, thereby effectively shielding these species from interacting with the electrode or ions in the sample. By preventing such interactions, the sensitivity and reliability of the electrochemical sensor of the present invention may be greatly increased.

The interfering species may be any redox active molecule. Preferably, the interfering species is a molecule with a similar, or substantially identical, redox profile to the analyte. The interfering species may have a similar structure and chemical properties to the analyte. Accordingly, if the binding agent were not present, the interfering species may affect the voltage and/or current which is measured, and thereby interfere with the detection of the analyte. The interfering species may be an acid, an organometallic complex, a metal ion complex, an organic redox active molecule, an electroconductive polymer, a metal ion, a nanoparticle containing a redox active centre and/or a gas. In some embodiments, the interfering species may be ascorbic acid, ferrocene or a derivative thereof, flavin or a derivative thereof, dopamine, humic acid, hydrogen peroxide, and/or oxygen.

The analyte may be any redox active molecule. Preferably, the analyte is a species which can be detected electrochemically, for instance by sensors and/or biosensors. Accordingly, the interfering species may be an acid, an organometallic complex, a metal ion complex, an organic redox active molecule, an electroconductive polymer, a metal ion, a nanoparticle containing a redox active centre or a gas. In some embodiments, the interfering species may be ascorbic acid, ferrocene or a derivative thereof, flavin or a derivative thereof, dopamine, humic acid, hydrogen peroxide, fructose, mannose, glucose or oxygen.

In an alternative embodiment, the interfering species may not be a redox active molecule. The interfering species may have a similar structure and chemical properties to the analyte. The interfering species may be an acid, an organometallic complex, a metal ion complex, an organic molecule, an electroconductive polymer, a metal ion, a nanoparticle and/or a gas. In some embodiments, the interfering species may comprise glucose, fructose and/or mannose.

In this embodiment, the analyte may also not be a redox active molecule. The analyte may be an organic molecule, a biological molecule or its metabolite, or a gas. In some embodiments, the analyte may comprise glucose, fructose or mannose.

Accordingly, the method may comprise disposing a mediating agent in the electrochemical compartment, wherein the mediating agent is configured to react with the analyte and thereby producing a redox active molecule.

It may be appreciated that the mediating agent may be disposed in the solution prior to the solution being disposed in the electrochemical compartment. Accordingly, the mediating agent will be transferred to the electrochemical compartment at the same time as the solution. Alternatively, the mediating agent may be disposed in the electrochemical compartment before or after the solution is disposed therein.

Preferably, the mediating agent is disposed in the solution and/or the electrochemical compartment before, after of together with the binding agent. Preferably, the mediating agent is disposed in the electrochemical compartment before a voltage is io applied across the electrodes. Advantageously, the binding agent prevents the interfering species from reacting with the mediating agent.

The mediating agent may comprise an enzyme, a transition metal compound, a metallocene derivative, a phenoxazine, a phenothiazine, a stable quinone or derivative thereof, and/or a species that in its oxidized state has a quinoid structure. Preferably, the mediating agent comprises an enzyme and a further molecule configured to donate or receive electrons. Accordingly, the enzyme may be configured to react with the analyte and to transfer or receive electrons to or from the further molecule to thereby produce a redox active molecule. The further molecule may comprise a transition metal compound, a metallocene derivative, a phenoxazine, a phenothiazine, a stable quinone or derivative thereof, and/or a species that in its oxidized state has a quinoid structure.

The enzyme may comprise glucose oxidase. The transition metal compounds may comprise an osmium, ruthenium, iron, or cobalt compound. The metallocene derivative may comprise ferrocene, ferrocyanide, ferricyanide, or an osmium or ruthenium transition metal complex. The phenoxazine may comprise 7-dimethylamino-1,2-benzophenoxazine, 1,2-benzophenoxazine, Nile Blue, Brilliant Cresyl Blue, tetramethylphenylenediamine, dichlorophenolindophenol, an N-methyl phenazonium salt, or a tetrazolium salt. The phenothiazine may comprise toluidine blue. The stable quinone may comprise naphthoquinone, phenoquinone, benzoquinone, naphthenequinone. The quinone derivative may comprise acenaphthenequinone or an ubiquinone. The species that in its oxidized state has a quinoid structure may comprise Nile Blue or indophenol. Alternatively, or additionally molecule configured to donate or receive electrons may comprise Taylor's blue (i.e., 1,9-dimethylmethylene blue), N,N'-diethylthiacyanine iodide, or thionine.

For instance, glucose does not generate an electrochemical signal in a biosensor in the absence of relevant enzyme-mediator system, such as glucose oxidase and ferrocene. However, if no binding agent is present, fructose and/or mannose present in the sample would also interact with the enzyme-mediator system, distorting the signal which is generated. However, when binding agents are present they will bind the fructose and mannose rendering them unavailable for the interaction with the enzyme-mediator system.

In some embodiments, the method may comprise disposing a plurality of binding agents in the electrochemical compartment. The plurality of binding agents may comprise at least two, at least three or at least four binging agents. Preferably, each binding agent is configured to bind to a different interfering species in the solution. Advantageously, the method of the first aspect can be used to supress the electrochemical signal of multiple interfering species.

Preferably, the binding agent has a dissociation constant ($K_D$) of less than 10 mM for the interfering species. More preferably, $K_D$ is less than 1 mM, less than 100 µM or less than 10 µM, and most preferably is less than 1 µM.

The binding agent may be disposed in the solution. Preferably, the concentration of the binding agent in the solution is the same as or higher than the concentration of the interfering species in the solution. Preferably, the concentration of the binding agent is at least 0.1 pM, more preferably at least 1 pM, at least 10 pM or at least 100 pM, most preferably at least 1 nM, at least 10 nM or at least 100 nM. Preferably, the concentration of the binding agent is less than 1 M, more preferably less than 100 mM, less than 10 mM or less than 1 mM, most preferably less than 100 µM, less than 10 µM or less than 1 µM. Preferably, the concentration of the binding agent is between 0.1 pM and 1 M, more preferably between 1 pM and 100 mM, between 10 pM and 10 mM or between 100 pM and 1 mM, most preferably between 1 nM and 100 µM, between 10 nM and 10 µM or between 100 nM and 1 µM.

The binding agent can be immobilised on a surface in the electrochemical compartment. The binding agent may be immobilised on the surface covalently or by physical adsorption. Alternatively, the binding agent may be entrapped in a gel or polymer which is disposed on the surface. The surface may comprise a surface of the electrode. Preferably, the number of molecules of the binding agent immobilised on the surface is the same as or higher than the number of molecules of the interfering species in the solution. Preferably, at least a monolayer of the binding agent is disposed on the surface of the electrode.

It may be appreciated that physical adsorption may be carried out by evaporating a solution of the binding agent on the electrode. Alternatively, covalent attachment can be achieved in different ways, depending on the chemistry of the binder and the electrode. For instance, the electrode may first be derivatised in a way that it would expose primary amine, carboxyl, thiol, epoxy, azide, alkyne, or hydroxyl groups, and the binding agent may then be covalently attached thereto.

Alternatively, the binding agent can be entrapped in a membrane. Preferably, the number of molecules of the binding agent entrapped in the membrane is the same as or higher than the number of molecules of the interfering species in the solution.

It may be appreciated that the binding agent may be incorporated in a porous membrane by solvent evaporation in the presence of suitable polymers, such as PVC or cellulose.

Preferably, the binding agent has a dissociation constant ($K_D$) of at least 100 nM for the analyte. More preferably, $K_D$ is at least 1 mM, at least 10 mM or at least 100 mM, and most preferably at least 1M.

In one embodiment, the analyte is dopamine and the interfering species is ascorbic acid. In another embodiment, the analyte is glucose and the interfering species is fructose and/or mannose, preferably fructose and mannose.

The sample may be a biological sample. Preferably, the biological sample is taken from an animal or human, most preferably a human. Accordingly, the sample may be a blood sample, a urine sample or a serum sample.

The sample may be a food or drink sample. Accordingly, the sample may comprise a food or drink sample designed to be consumed by a human or animal.

The sample may be an environmental sample. Accordingly, the sample may be a water sample, a soil sample or an air sample.

The solution may further comprise a solvent. The solvent may comprise a buffer. It may be appreciated that the buffer which is selected will vary depending upon the analyte to be detected. In one embodiment, the buffer may comprise phosphate-buffered saline (PBS). The ratio of the sample to the solvent may be between 1:1000 and 1:1, preferably between 1:500 and 1:10, between 1:250 and 1:20 or between 1:100 and 1:25, more preferably between 1:80 and 1:30, between 1:70 and 1:35 or between 1:60 and 1:40.

The present invention extends to a kit which may be used to detect an analyte.

In accordance with a second aspect, there is provided a kit for detecting an analyte in a sample, the kit comprising:
- an electrochemical cell comprising an electrochemical compartment configured to receive a solution comprising a sample to be tested, wherein the sample comprises an analyte and an interfering species, and first and second spaced apart electrodes configured to be disposed in the solution; and
- a binding agent configured to bind to the interfering species,
- wherein the electrochemical cell is configured to apply a voltage across the first and second electrodes and thereby causing a current to flow through the first and second electrodes and a solution disposed in the electrochemical compartment and the electrochemical cell is further configured to measure the current and/or voltage, and thereby detect the analyte.

Preferably, the kit is used to conduct the method of the first aspect.

Preferably, the solution, the sample, the binding agent, the interfering species and the analyte are as defined in relation to the first aspect.

The kit may comprise a power supply configured to apply a voltage across the first and second electrodes. The power supply could comprise a battery, a generator, a renewable power source or it could comprise the national grid.

The kit may comprise an ammeter configured to measure a current flowing through the first and second electrodes and a solution disposed in the electrochemical compartment. The kit may comprise a voltmeter configured to measure the potential difference between the first and second electrodes. The kit may comprise a signal processor, configured to measure, filter or compress the signals produced by the ammeter and/or voltmeter.

The kit may further comprise a display configured to display the current and/or voltage measured.

The kit preferably comprises a potentiostat. Preferably, the potentiostat is configured to control the voltage applied across the first and second electrodes.

The kit may comprise three or more electrodes. In some embodiments, one of the electrodes is a reference electrode.

The electrodes may comprise carbon, a metal and/or silicon. Accordingly, the electrodes may comprise carbon paste electrodes, screen-printed carbon electrodes, glassy carbon electrodes, gold electrodes, platinum electrodes, carbon nanotube electrodes, indium tin oxide electrodes, silicon electrodes, aluminium electrodes, copper electrodes, or silver electrodes.

One or more of the electrodes may comprise a coating. The coating may comprise a polymer, bovine serum albumin or polyethylene glycol. Advantageously, the coating further decreases non-specific binding or formation of surface contamination using techniques described in the art.

All of the features described herein (including any accompanying claims, abstract and drawings), and/or all of the steps of any method or process so disclosed, may be combined with any of the above aspects in any combination, except combinations where at least some of such features and/or steps are mutually exclusive.

For a better understanding of the invention, and to show how embodiments of the same may be carried into effect, reference will now be made, by way of example, to the accompanying Figures, in which.

EXAMPLES

Methods

The protocol for the preparation of ascorbic acid modified solid-phase was adapted from Canfarotta et al. Briefly, glass beads were activated by boiling them in NaOH (4 M) for 10 min and washed with DI water and acetone. After drying in the oven at 80° C. overnight, the beads were incubated in a 2% v/v solution of GOPTS (3-glycidyloxypropyl trimethoxysilane) in anhydrous toluene, containing also N-ethyldiisopropylamine 2 mg/mL, at 55° C. for 5 h. Afterwards, the glass beads were poured into a Buchner funnel, rinsed with toluene twice, then with acetone (800 mL) and eventually dried under vacuum. These epoxy-functionalised beads were then incubated in a solution of ascorbic acid 2 mg/mL in PBS 0.01 M pH 7.2 overnight. Finally, the glass beads were filtered and rinsed with water (800 mL water for 150 g beads), dried under vacuum and stored under inert atmosphere ($N_2$) at 4° C. until use.

To synthesise nanoMIPs imprinted against ascorbic acid, a polymerisation in PBS was performed. In particular, N-isopropylacrylamide (Sigma-Aldrich) (39 mg), N-tert-butylacrylamide (Sigma-Aldrich) (33 mg), N-(3-aminopropyl)methacrylamide hydrochloride (Polysciences, Inc.) (5.8 mg), acrylic acid (Sigma-Aldrich) (2.2 µL), and N,N'-methylenebisacrylamide (Sigma-Aldrich) (2 mg) were dissolved in 100 ml PBS. Prior to initiating the polymerisation process, the mixture was purged with $N_2$ and sonicated for 30 min. At the same time, functionalised beads were purged with $N_2$ for 20 min. The beads were then added to the polymerisation solution and purged with $N_2$ for 5 min. The mixture of beads and polymerisation solution was swirled gently and then the polymerisation was started by adding ammonium persulfate (APS) (60 mg/ml) and N,N,N',N'-tetramethylethylenediamine (TEMED) (22 μL) as catalysts. The polymerisation was performed overnight at room temperature, after flushing the headspace of the bottle used for the reaction with $N_2$ for 30 seconds. The following day, the beads were washed with deionised water, following the steps described by Canfarotta et al., by using a 60 mL solid-phase extraction (SPE) cartridge fitted with a frit of 20 μm porosity. Afterwards, the high-affinity nanoMIPs were eluted at 65° C. with deionised water, until a total volume of 100 mL of solution was obtained.

Typically, the nanoMIPs produced using the above method have a dissociation constant in the nanomolar range e.g. between 0.1 and 1000 nM.

Multi-Pulsed Amperometry (MPA)

Cyclic Voltammetry (CV) was performed to obtain the value of oxidation potentials of the chosen electroactive molecules, setting the following parameters: scan range from −0.6 V to +0.5 V, step potential of 0.025 V, scan rate 0.1 V/s. Measurements were performed using the screen printed cells as a drop on cell, placing 50 μL of solution onto the electrodes surfaces and performing the scans.

Multi-pulsed Amperometry (MPA) was performed adapting the procedure described by Takátsy et al. by setting the following parameters:

number of pulses 2,
$E_{pulse1}$ 0.250 V,
$E_{pulse2}$ 0 V,
$t_{pulse1}$ 0.2 sec, and
$t_{pulse2}$ 1.5 sec.

Current was recorded during the application of $E_{pulse1}$. Measurements were performed immersing the screen printed cell into a 5 mL sample solution under stirring.

All reported potentials refer to the pseudo-reference silver electrode and the measurements were performed at room temperature.

Amperometric measurements based on the oxidation of electroactive targets at the electrode surface were carried out continuously. Volumes of ascorbic acid and dopamine solutions were directly added from buffered 100 82 M stock solutions to the 5 mL volume sample solution kept under stirring. Total volume variation was neglected. Tested concentrations were within 50-550 nM and 12-35 μM for ascorbic acid (AA) and 100-500 nM for dopamine (DA). Current increases after each addition were taken as analytical signal, reporting $\Delta(i-i_o)$ versus analyte concentration. All measurements were carried out in PBS pH=7.2 buffered solutions or PBS pH=7.2 diluted matrices.

Electrochemical measurements carried out for ascorbic acid and dopamine were repeated in PBS pH=7.2 buffered solutions containing the synthesised nanoMIPs, in order to investigate their ability to selectively suppress ascorbic acid oxidation signal. Current increases after each addition were considered as analytical signal, reporting $\Delta(i_{MIP}-i_{oMIP})$ versus analyte concentration and comparing them to those previously obtained in PBS pH=7.2 buffered solutions without nanoMIPs. Per cent decrease of current increases after every analyte addition was also used to evaluate signal suppression.

For all of the experiments described, the concentration of the nanoMIPs in solution was 0.1 mg/ml. However, it will be appreciated that other concentrations could be used.

Figure 1:
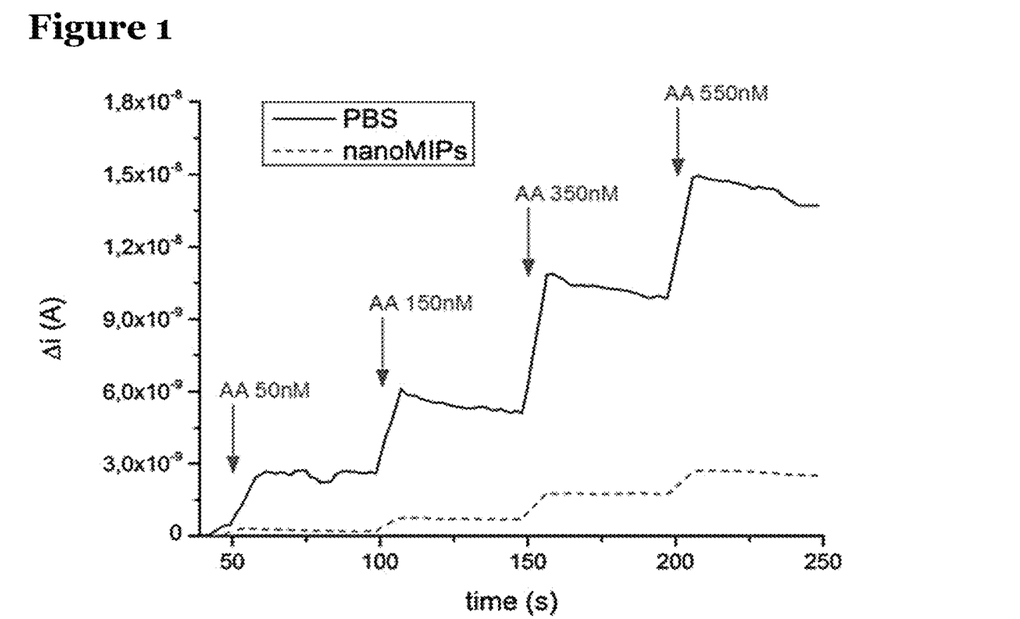
FIG. 1 is a graph showing recorded chrono-amperograms. Current values are recorded continuously and plotted against time. The ascorbic acid (AA) concentration is highlighted after every addition. $\Delta i$ values refer to the difference $i_x - i_{blank}$ where x is the concentration of AA in the sample solution after each addition and $i_{blank}$ refers to the current value recorded when no AA is present.
Figure 2:
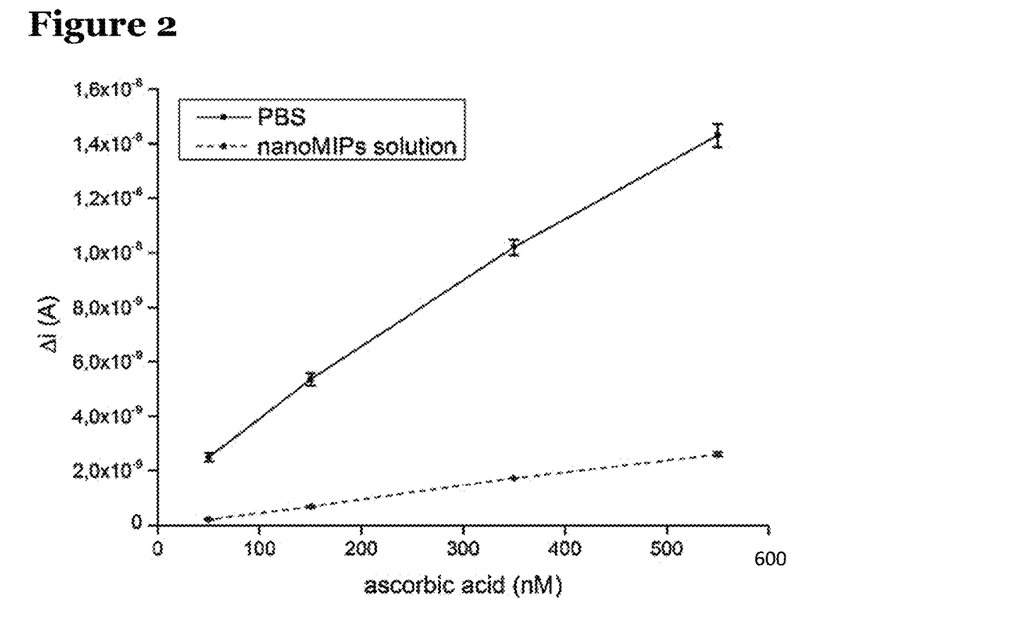
FIG. 2 is a graph showing how the recorded current values change as the concentration of ascorbic acid (AA) varies in sample solutions. $\Delta i$ values refer to the difference $i_x - i_{blank}$ where x is the concentration of AA in the sample solution after each addition and $i_{blank}$ refers to the current value recorded when no AA is present.

Example 1—Quantitative Electrochemical Suppression of Ascorbic Acid Oxidation Current For proof of concept purposes, the inventors explored the possibility of applying the proposed method for suppressing interfering currents in sensing devices. To this end, analysis of ascorbic acid was performed in the nanomolar range, from 50 nM to 550 nM, see FIGS. 1 and 2. Current response of tested AA concentrations in PBS buffered solution was compared to measurements carried out in nanoMIPs solution, obtaining a quantitative current suppression for AA concentrations close to the lower limit of 50 nM.

Figure 3:
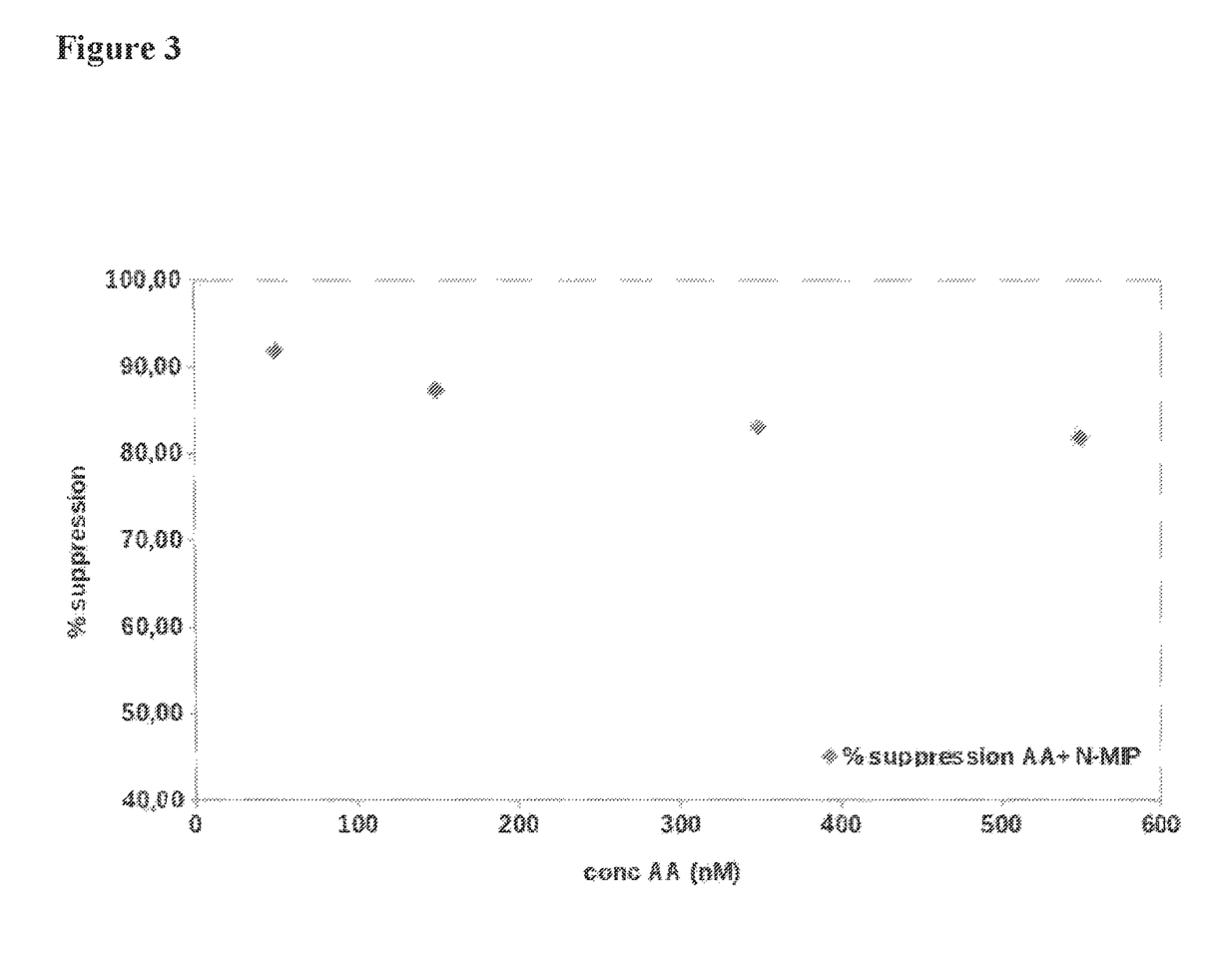
FIG. 3 is a graph showing the % suppression of AA by the nanoMIPs.

The amount the current reading was suppressed by using the nanoMIPs was calculated as a percentage. Values of ≥90% were achieved for AA concentrations lower than 100 nM and values of ≤90% were achieved for all other AA concentrations, see FIG. 3.

The inventors believe that higher concentrations of MIPs could further suppress the signal caused by AA.

Example 2—Dopamine Measurements

Measurements of dopamine (DA) were carried out in order to assess whether DA could be detected even in the presence of an interfering concentration of ascorbic acid, avoiding any sample pretreatment. Current response to subsequent DA additions in PBS solution was analyzed in the range 100-500 nM and then repeated in the presence of 50 nM and 100 nM AA. The experiment was then repeated in a nanoMIP solution.

Figure 4:
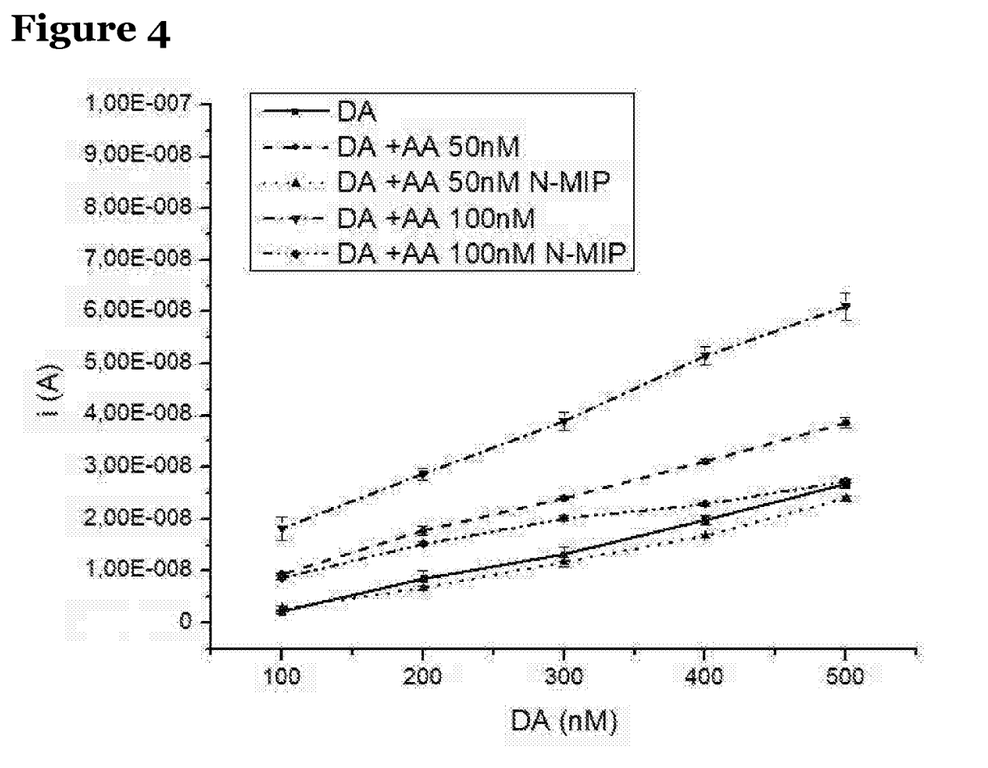
FIG. 4 is a graph showing how the recorded current values change as the concentration of dopamine varies in sample solutions. $\Delta i$ values refer to the difference $i_x - i_{blank}$ where x is the concentration of dopamine in the sample solution after each addition and $i_{blank}$ refers to the current value recorded when no dopamine is present.

The results, shown in FIG. 4 clearly show that the synthesized nanoMIPs were able to selectively suppress AA interfering current in an electrochemical detection of DA in PBS. The maximum AA concentration that could be quantitatively sequestered with the described setup was 50 nM, allowing the inventors to correctly determining DA, without any other sample pretreatment. Again, the inventors believe that higher concentrations of MIPs could suppress the signal caused by AA at a concentration of greater than 50 nM.

Example 3—Real Samples

The proposed method was then applied to analyze DA in real samples. Measurements were carried out in diluted human serum samples, applying the same experimental setup already described, and the results are showed in FIG. 5.

Figure 5:
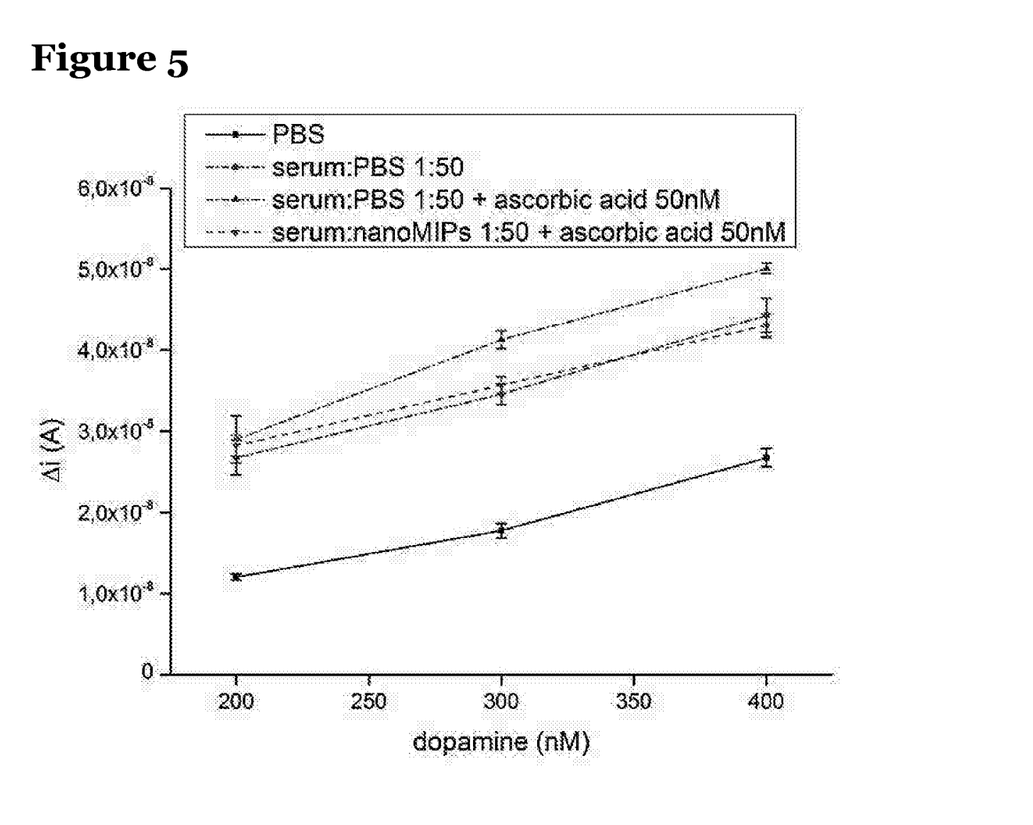
FIG. 5 is a graph showing how the recorded current values change as the concentration of dopamine varies in sample solutions. $\Delta i$ values refer to the difference $i_x - i_{blank}$ where x is the concentration of dopamine in the sample solution after each addition and $i_{blank}$ refers to the current value recorded when no dopamine is present.

In a complex matrix, interfering current generated by the presence of a fixed concentration of AA is still capable of affecting measurements, leading to errors in DA detection. However, as shown in FIG. 5, nanoMIPs were able to suppress interfering current, thus proving their suitability as novel analytical tools for the electrochemical suppression of potential interfering species.

Conclusion

The inventors have shown that they can use nanoMIPs to suppress signals from interfering species, and allow analytes to be accurately detected using amperometry.

REFERENCES

[1] Molecularly imprinted polymer sensors (WO2015130529 A3). Belbruno, 2015.
[2] Molecular imprinted nanosensors (U.S. Pat. No. 9,134,305 B2). Cai et al., 2012.

[3] Methods and apparatus for the fabrication and use of graphene petal nanosheet structures (CA2845539 A1). Claussen et al., 2012.
[4] Molecular recognition sensor system (U.S. Pat. No. 6,807,842 B). Williams et al., 2003.
[5] Small Volume In Vitro Analyte Sensor (U.S. Pat. No. 9,234,864 B2). Heller et al., 2016.
[6] Disposable sensor for liquid samples (US2009050477 A). Catt et al., 2009.
[7] J. Wang, Chemical Reviews, 108 (2), 814-825, 2008.
[8] T. G. Drummond, M. G. Hill, J.K. Barton. Nature Biotechnology, 21(10), 1192-1199, 2003.
[9] K. Cammann, W. Kleiböhmer, E. Mussenbrock, B. Roß, F. Zuther. Fresenius' Journal of Analytical Chemistry, 349 (5), 338-345, 994
[10] I. Volov, O. Mann, Y. Hoenersch, B. Wahl, A.C. West. Journal of Separation Science, 34 (18), 2385-2390, 2011.
[11] S. Koide, Y. Kinoshita, N. Ito, J. Kimura, K. Yokoyama, I. Karube. Journal of Chromatography B: Analytical Technologies in the Biomedical and Life Sciences 878 (23), 2163-2167, 2010.
[12] E. Paleček, M. Fojta. Talanta 74 (3), 276-290, 2007.
[13] D. J. Daly, C. K. O'Sullivan, G. G. Guilbault. Talanta 49, 667-678, 1999.
[14] F. Canfarotta, A. Poma, A. Guerreiro, S. Piletsky, Nat. Protocols, 11: 443-455, 2016.

The invention claimed is:

1. A method of detecting an analyte in a sample, the method comprising:
   disposing a binding agent in an electrochemical compartment, wherein the binding agent is configured to bind to an interfering species and the binding agent comprises a molecularly imprinted polymer (MIP);
   disposing a solution comprising a sample in the electrochemical compartment, wherein the sample comprises an analyte and the interfering species;
   applying a voltage across first and second spaced apart electrodes disposed in the solution, and thereby causing a current to flow through the solution between the electrodes, wherein the binding agent is also disposed in the solution, such that the solution comprises the binding agent; and
   measuring the current and/or voltage and thereby detecting the analyte.

2. The method according to claim 1, wherein the method comprises measuring the current and thereby detecting the concentration of the analyte in the solution.

3. The method according to claim 1, wherein the MIP comprises a microparticle, a nanoparticle, and/or a linear MIP.

4. The method according to claim 1, wherein the interfering species and the analyte are redox active molecules, and wherein the interfering species has a similar redox profile to the analyte.

5. The method according to claim 1, wherein the interfering species is an acid, an organometallic complex, a metal ion complex, an organic redox active molecule, an electroconductive polymer, a metal ion, a nanoparticle containing a redox active centre and/or a gas.

6. The method according to claim 5, wherein the interfering species is ascorbic acid, ferrocene or a derivative thereof, flavin or a derivative thereof, dopamine, humic acid, hydrogen peroxide and/or oxygen.

7. The method according to claim 1, wherein the interfering species and the analyte are not redox active molecules, and wherein the interfering species has a similar structure and chemical properties to the analyte.

8. The method according to claim 7, wherein the method comprises disposing a mediating agent in the electrochemical compartment, and wherein the mediating agent is configured to react with the analyte and thereby produces a redox active molecule.

9. The method according to claim 8, wherein the mediating agent comprises an enzyme and a molecule configured to donate or receive electrons.

10. The method according to claim 1, wherein the binding agent has a dissociation constant ($K_D$) of less than 10 mM for the interfering species.

11. The according to claim 1, wherein the concentration of the binding agent in the solution is the same as or higher than the concentration of the interfering species in the solution.

12. The method according to claim 1, wherein the sample is a biological sample, a food or drink sample or an environmental sample.

13. The method according to claim 1, wherein the binding agent is disposed freely in the solution.

14. The method according to claim 1, wherein the binding agent is disposed in the solution at a concentration between 0.1 pM and 1 M.

15. A kit for detecting an analyte in a sample, the kit comprising:
   an electrochemical cell comprising an electrochemical compartment configured to receive a solution comprising a sample to be tested, wherein the sample comprises an analyte and an interfering species, and first and second spaced apart electrodes configured to be disposed in the solution; and
   a binding agent comprising a molecularly imprinted polymer (MIP) and configured to bind an interfering species and be disposed in the solution, such that the solution comprises the binding agent;
   wherein the electrochemical cell is configured to apply a voltage across the first and second electrodes thereby causing a current to flow through the first and second electrodes and the solution disposed in the electrochemical compartment and wherein the electrochemical cell is further configured to measure the current and/or voltage, and thereby detect the analyte.

16. The kit according to claim 15, wherein the kit further comprises a power supply configured to apply a voltage across the first and second electrodes.

17. The kit according to claim 15, wherein the kit further comprises an ammeter configured to measure a current flowing through the first and second electrodes and the solution disposed in the electrochemical compartment.

18. The kit according to claim 17, wherein the kit further comprises a signal processor that is configured to measure, filter or compress the signals produced by the ammeter.

19. The kit according to claims 15, wherein the kit further comprises a potentiostat.

20. The kit according to claim 15, wherein the MIP comprises a microparticle, a nanoparticle and/or a linear MIP.

21. The kit according to claim 15, wherein the binding agent is configured to be disposed in the solution at a concentration of at least 0.1 pM.

* * * * *